United States Patent [19]

Silverbåge

[11] 4,229,105

[45] Oct. 21, 1980

[54] SENSITIVE MEASURING CELL FOR A DIFFERENTIAL REFRACTOMETER OF THE INTERFERENCE TYPE

[76] Inventor: Sten Silverbåge, Bergencrantz väg 6, 196 30 Kungsängen, Sweden

[21] Appl. No.: 29,401

[22] Filed: Apr. 12, 1979

[30] Foreign Application Priority Data

Apr. 17, 1978 [SE] Sweden ............................ 7804340

[51] Int. Cl.³ ............................................. G01N 1/10
[52] U.S. Cl. ................................... 356/246; 356/130; 356/361
[58] Field of Search ................ 356/246, 361, 130–132

[56] References Cited

U.S. PATENT DOCUMENTS

| | | | |
|---|---|---|---|
| 2,964,992 | 12/1960 | Hordle | 356/246 |
| 3,680,963 | 8/1972 | Edwards et al. | 356/361 |

FOREIGN PATENT DOCUMENTS 569274  11/1975  Switzerland .

*Primary Examiner*—John K. Corbin
*Assistant Examiner*—Bruce Y. Arnold
*Attorney, Agent, or Firm*—Sughrue, Rothwell, Mion, Zinn and Macpeak

[57] ABSTRACT

A highly sensitive measuring cell for a differential refractometer of the interference type for chemical analyzers comprises two channels in a measuring body, one of said channels conveying a medium whose refractive index is to be measured and the other channel conveying a reference medium of known refractive index. The respective path lengths of the measuring channel and the reference channel are mechanically adjustable to exactly the same lengths in order that a maximum common mode rejection ratio (hereafter "CMRR") value may be achieved.

8 Claims, 3 Drawing Figures

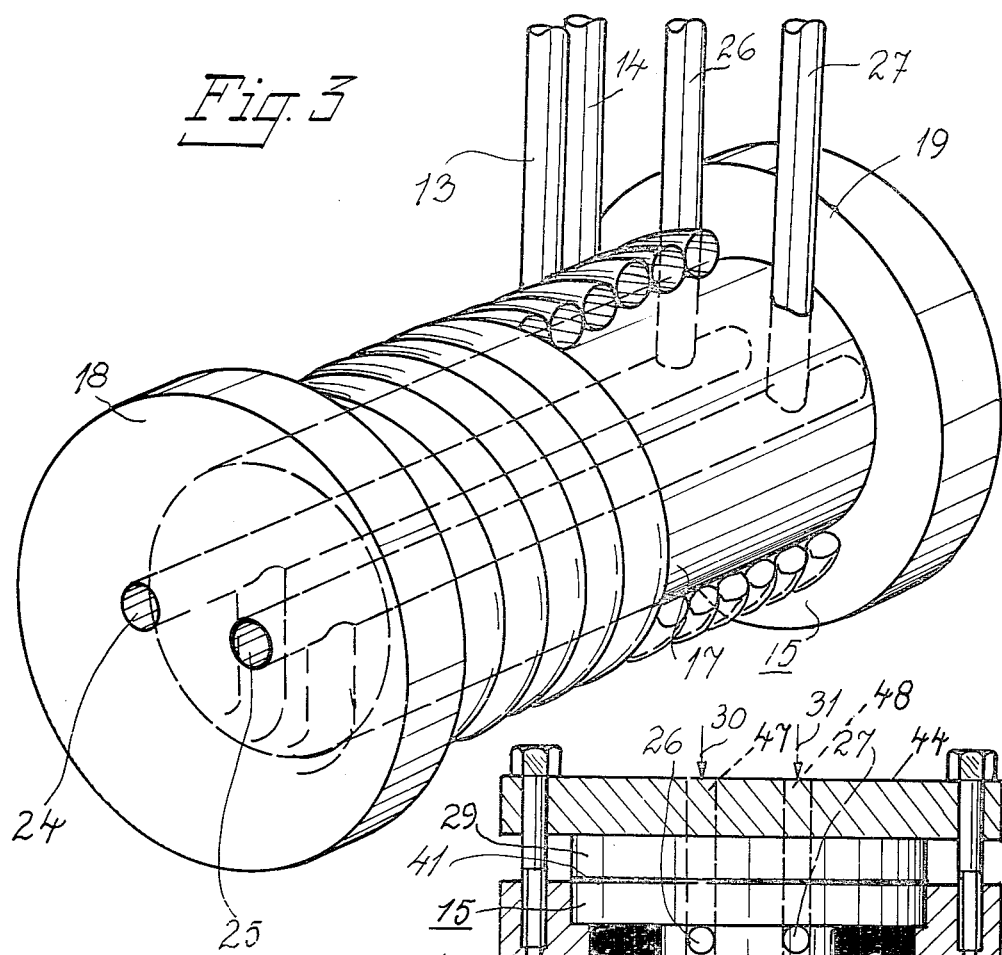
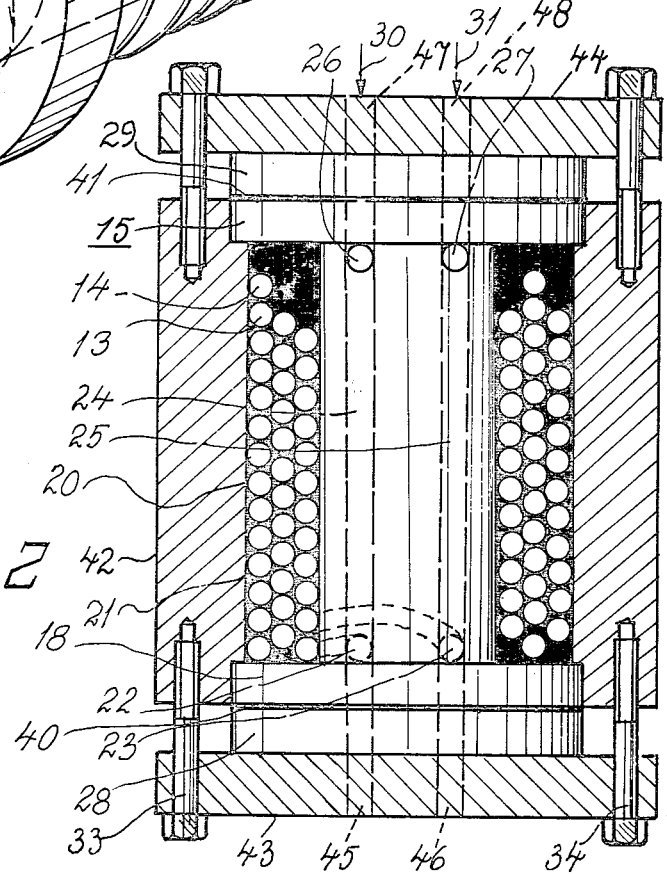

SENSITIVE MEASURING CELL FOR A DIFFERENTIAL REFRACTOMETER OF THE INTERFERENCE TYPE

BACKGROUND OF THE INVENTION

1. Field of the Invention

This invention refers to a highly sensitive measuring cell for a differential refractometer of the interference type or other type of detector for chemical analyzers.

2. Description of the Prior Art

It is known that an indicator of the concentration of a liquid or gaseous sample can be obtained by measuring its refractive index. However, with increasing requirements for measuring low concentrations it becomes more and more important to maintain the temperature and the pressure constant. Nevertheless, as the concentration is decreased a limit is soon reached, beyond which it is not possible to maintain the temperature and pressure constant by conventional methods.

By performing differential measurement on the basis of a known sample and an unknown sample, it is possible to drastically reduce the constant temperature and pressure requirements, as both of the samples subjected to measurements are affected by temperature and pressure to an equal degree. Various types of refractometers which are based on this principle are available, and they may for example either utilize two prismatic cells for the samples or may utilize two cells for measuring total reflection, with the last-mentioned cells being disposed such that when the same refractive index exists in the two cells the deflection of light passing through the cells will not be affected. These refractometers are of the diffraction type.

In recent years a refractometer of the interference type has also entered the market. This refractometer operates by measuring the velocity of light through the measuring cell and through the reference cell whereafter the difference in velocities is determined. In this manner it becomes theoretically possible to increase the sensitivity to a great extent in consequence of the signal to noise ratio of a refractometer operating on the interference principle being high, but of course the requirements with regard to the measuring cell will become higher to a corresponding degree.

SUMMARY OF THE INVENTION

Thus, this invention refers to a measuring cell which is intended to be used in a differential refractometer of the interference type. As the result of this measuring cell it is possible to increase the sensitivity of the refractometer very substantially as compared to other designs. The importance of this is obvious in connection with measuring for example small amounts of impurities in water and in other liquids as well as in gases.

The measuring cell proposed by this invention is designed such that, when it is utilized together with a differential refractometer, the differential qualities will be safeguarded to the maximum extent.

Thus, an equalization of temperature between the measuring medium and the reference medium will be provided in the measuring cell proper so that exactly the same temperature will be at hand in the measuring space as in the reference space. This is carried out in such manner that the measuring medium which is to be supplied to the measuring space firstly is passed around the reference space in a tube having good thermal contact with the measuring space. The supply to the reference space circulates the measuring space in the same manner.

By means of an appropriate design of the inlets it becomes possible to provide exactly the correct compensation for each given flux velocity and heat capacity, respectively, of the relevant medium, i.e. neither subcompensation nor over-compensation.

Furthermore, equalization of pressure between the measuring and reference spaces is carried out by the outlets from the measuring and reference spaces being brought together either in the measuring cell proper or by a T-junction outside the cell. In consequence of the manner in which temperature compensation is carried out as above, pressure equalization can be achieved without the temperature compensation being lost.

Finally, the device is designed such that disturbing temperature influences from the environment do not affect the measuring cell and such that the accuracy with which thermostat control is carried out does not affect the measuring results. In consequence of the measuring and reference spaces being placed in a thermostatically controlled area but insulated from the latter, the temperature of the measuring space will substantially be a function of the temperature of the measuring medium as the result of the measuring space having small thermal capacity because of its small mass. The temperatures in the thermostatically controlled measuring space and in the reference medium should of course not differ to a substantial extent. Therefore, both the measuring medium and the reference medium are thermostatically controlled before they are supplied to the thermostatically controlled measuring space.

Thus, according to the invention a device is provided wherein a measuring and/or reference medium, which is thermostatically controlled beforehand by means of the heat capacity of the device itself, equalizes short-term variations in the thermostatically controlled measuring flux. The absolute temperature of the measuring flux is directly dependent on the accuracy of the thermostat, and the control error in said thermostat is propagated directly to the measuring and reference media. By means of this device control errors of a short-term character (on-off control) are equalized so that they are reduced to the measuring/reference spaces.

The most essential advantage of the methods disclosed by the invention is that a measuring system for gases and liquids is achieved in which the concentration differences in the ppb level can be measured with great exactness. The method is an accurate one and it is physically correct as well as simple, and the total apparatus cost is low as compared to other measuring methods which are utilized for these sensitivity levels.

During the work which has led up to the present invention it has been found that in order to be able to utilize the above-mentioned advantages of temperature equalization, pressure equalization and design of the device in such a manner that disturbing temperature influences from the environment do not affect the measuring cell and the thermostat control exactness does not affect the measuring results, the cell has to have a very high CMRR value. This designation is normally utilized in electronic relationships and means "Common Mode Rejection Ratio." CMRR is measured in decibels and is defined as 20 log (N/$\Delta$n), wherein N is the absolute refractive index of the relevant medium and $\Delta$n is the difference between the N-values in the measuring and reference channels, respectively.

The basis of the compensation in the above-mentioned measuring cell design is that, if an error occurs, the same error will be introduced into both of the cells so that the errors cancel each other. If the CMRR value of the cell is low then the compensation will be correspondingly poor.

According to the present invention two methods have been developed for trimming a measuring cell in a differential refractometer so that the highest possible CMRR value is achieved, namely the following:

(a) In refractometers of the interference type the optical paths of the two cells with the same medium (same refractive index) in the measuring space as in the reference space are set to the same geometrical length by mechanical adjustment. The trimming can be performed up to a fraction of the wavelength of light and is very accurate.

(b) The angles of a prismatic cell or a total reflection cell are adjusted such that the reading of the differential refractometer is affected to the smallest possible extent when media having differing refractive indices are introduced into the two cells simultaneously. Hereby a maximum CMRR value is achieved for these cells.

Basically the same adjustment can be carried out on a measuring cell of a refractometer of the interference type, wherein the lengths of the respective measuring spaces are adjusted instead.

DESCRIPTION OF THE DRAWINGS

The invention will be described more specifically below with reference to the accompanying drawings, in which FIG. 2 shows a sectional view of a measuring body included in the measuring cell of FIG. 1, and FIG. 3 is an isometric view of a bobbin included in the measuring body in accordance with FIG. 2.

The same reference numerals have been utilized in the various figures wherever possible.

DESCRIPTION OF THE PREFERRED EMBODIMENT

Figure 1:
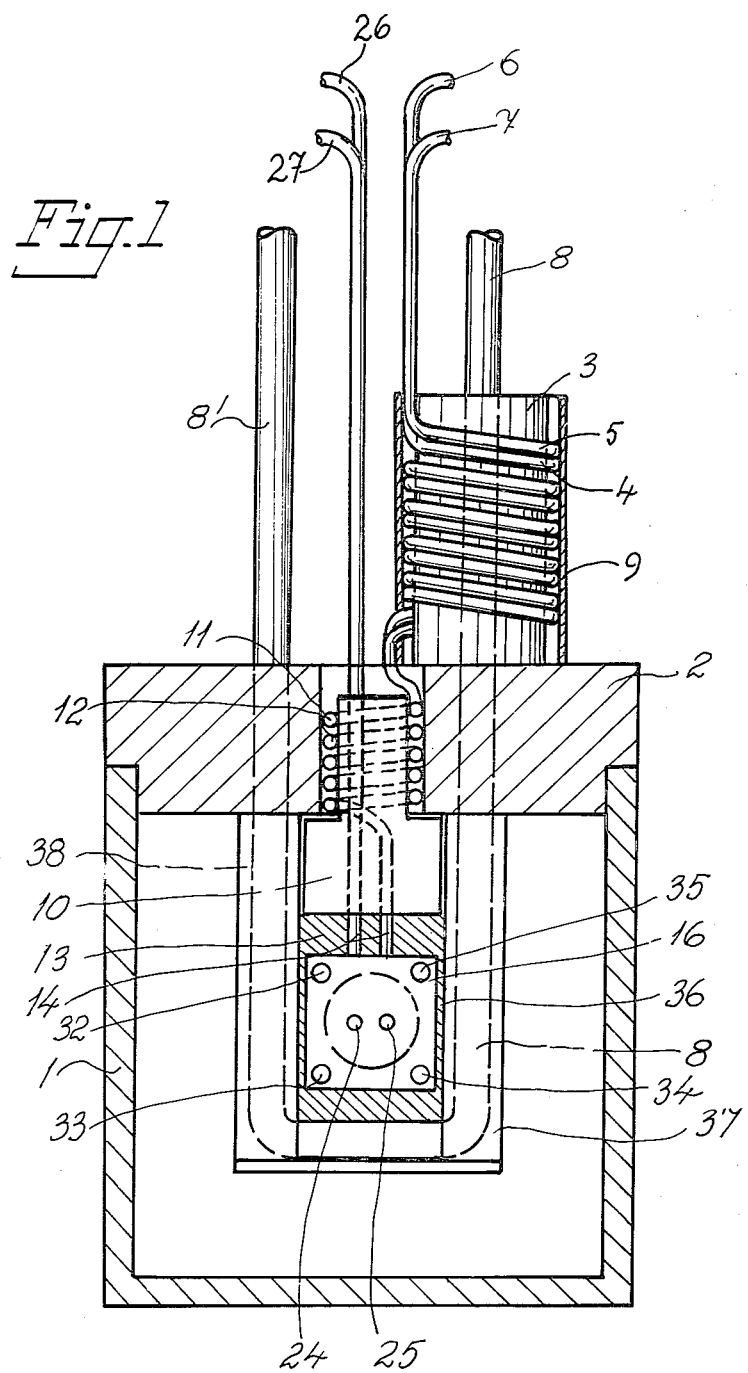
FIG. 1 illustrates a front view, partly in section, of a measuring cell in accordance with the invention introduced into a refractometer of the interference type.

FIG. 1 shows a measuring cell in accordance with the invention introduced into a refractometer of the interference type, wherein the walls of the refractometer are designated 1. Readout of said refractometer is performed by means of a photomultiplier (not shown) in a manner known per se.

The measuring cell comprises a cap 2, which, for example, may be cylindrical and which mates with the refractometer and supports a thermostat control block 3 on its top, said block being surrounded by coils 4 and 5, through one of which the medium with regard to which measuring is carried out flows and is supplied through an inlet 6, and through the other of which a reference medium flows which is supplied through an inlet 7. The thermostat control block 3 is also penetrated, either centrally in its longitudinal direction or in some other appropriate manner, by a lead 8 for a thermostat controlling agent, for instance a liquid having an accurately controlled temperature. The block 3 is surrounded by an appropriate heat-insulating layer 9 outside of the coils 4 and 5. The thermostat control block 3 serves the purpose of ensuring that the inflowing flux has a substantially constant temperature.

The cap 2 of the measuring cell also carries a thermal capacitor 10, for example a piece of metal, having high thermal capacity for equalizing variations of the thermostat, and said thermal capacitor 10 is partially surrounded by coils 11 and 12 which comprise a continuation of the respective coils 4 and 5, with the propagated flux in the coils 11 and 12 having a temperature which is constant with regard to short-term variations of the thermostat.

The respective coils 11 and 12 continue from the thermal capacitor 10 down into a measuring body 16, with only the foremost lead, which is designated 14, being visible in FIG. 1.

The measuring body 16 is shown in cross section in FIG. 2 and includes a bobbin 15 which may be composed of metal and which is shown in an isometric view in FIG. 3. Bobbin 15 has a coil-shaped portion 17 and end walls 18 and 19. The continuations of the leads from coils 11 and 12 of the thermal capacitor 10 form coils outside of the metal bobbin 17 and are in close thermal engagement therewith. The relevant leads are designated 13 and 14, respectively, in FIG. 2, and they are designated 13 and 14 as inlets to the bobbin in FIG. 3. In order that the thermal transition shall be as good as possible leads 13 and 14 are molded into a tin mass 20 which engages the bobbin 17 and the leads 13 and 14 thereon and which forms a cylinder having the external wall 21.

The measuring medium and the reference medium, respectively, flow down to the lower portion of bobbin 17, as viewed in FIG. 2, and thereafter at the connection points 22 and 23 they each flow into an individual elongate channel 24 and 25, respectively, in metal bobbin 17 and along these channels to the respective outlets 26 and 27, which also are shown in FIG. 3.

Circular glass discs 28 and 29 are in close engagement with the individual circular end walls 18 and 19, respectively, of the bobbin over interleaved gaskets 40 and 41, and as the result of the resiliency of the gaskets these glass discs make it possible to precisely adjust the lengths of channels 24 and 25, which are utilized in the refractometer in carrying out measurements. This is done by light being introduced from the interferometer as indicated by the arrows 30 and 31. This light will pass through channels 24 and 25, which as has been mentioned above also are passed by the measuring medium and the reference medium. The gaskets 40 and 41 are provided with apertures corresponding to channels 24 and 25, which are seen from their ends in FIGS. 1 and 3.

The gaskets 40 and 41 provide the above-mentioned capability of adjusting channels 24 and 25 to the same lengths by urging the glass discs 28 and 29 with different pressures against the end walls 18 and 19 of the bobbin at different positions. For example, this can be done by means of screws 32, 33, 34 and 35, which are illustrated in the front surface of the measuring body 16 in FIG. 1. Two of said screws, namely 33 and 34, are also illustrated in FIG. 2, which shows that corresponding screws are also located at the rear surface of the measuring body. In order to secure the screws the entire unit comprising the bobbin with the surrounding coils and the end walls, gaskets and discs is placed in a casing 42, and the glass discs are tightened by means of end plates 43 and 44 which are penetrated by elongate openings 45–48 so that it is possible to look through channels 24 and 25.

For clarification of the above-mentioned adjustment of the channel lengths it should be mentioned that this is carried out by introducing the same medium into the measuring channel 24 as into the reference channel 25 and thereafter adjusting the interferometer to the order of 0 by means of the screws 32-35 at one end of the measuring cell and the corresponding screws at the other end. The interferometer and the glass plates have already previously been adjusted to the order of 0. In consequence of the adjustment just described the maximum CMRR value is achieved.

As is illustrated in FIG. 1 the measuring body 16 is floatingly disposed in the measuring cell, i.e. it is embedded and supported by an appropriate thermally insulating material 36. FIG. 1 also shows that the thermostat controlled lead 8 continues down through a block 37 which surrounds the thermally insulating medium 36 in which measuring body 16 is located, whereafter lead 8 first turns off horizontally and thereafter vertically so as to pass through another block 38 on its way back to the thermostat through lead 8'. In consequence of blocks 37 and 38 and thermal capacitor 10 as well as the insulation 36 surrounding the measuring body 16, and in addition caps (not shown) in front of and behind blocks 37 and 38, measuring body 16 will have a very constant temperature which is independent of the environment and the thermostat, which to a great extent contributes to the good measuring results.

The invention is not restricted to the embodiment described above and illustrated in the drawings, and this embodiment merely constitutes an example of the invention and its mode of utilization. For instance, the invention may also be applied to photometers, fluorometers, and other measuring instruments for chemical analyses of gases and liquids.

I claim:

1. A highly sensitive measuring cell for an interference type of differential refractometer, said measuring cell comprising:
    (a) a measuring body provided with two channels,
    (b) one of said channels being a measuring channel for a medium whose refractive index is to be measured, and
    (c) the other measuring channel being a reference channel for a reference medium of a known refractive index, and
    (d) means for mechanically adjusting the respective path lengths of said measuring channel and of said reference channel to exactly the same geometrical length for achieving a maximum CMRR value.

2. A measuring cell in accordance with claim 1, wherein said adjustment is carried out by the geometry of the measuring body being changed in an interferometer in which the measuring body is disposed,
with a medium introduced simultaneously into the two channels of the measuring body and having a different refractive index from that of the measuring medium, thus leaving the adjustment of the interferometer unaffected.

3. A measuring cell in accordance with claim 1, wherein said measuring body is formed by a metal block having a cylindrical cavity,
said cylindrical cavity being provided with a metal bobbin,
said metal bobbin being penetrated by channels and being surrounded by coil loops of such lengths that the best temperature compensation is achieved and through which the measuring medium and the reference medium, respectively, flow,
said coil loops each having an inlet and an outlet,
said outlet being connected to one end of each of said channels,
with the other ends of said channels comprising outlets for the measuring medium and for the reference medium, respectively.

4. A measuring cell in accordance with claim 3, wherein said coil loops for the measuring medium and for the reference medium, respectively, are molded into a thermally conductive substance, such as a tin mass.

5. A measuring cell in accordance with claim 4, wherein the measuring body of said cell is disposed in an environment having an accurately controlled temperature and pressure, said measuring channel being adapted to convey a measuring medium having an accurately controlled temperature, said reference channel being adapted to convey a reference medium having an accurately controlled temperature, and both said measuring channel and said reference channel being adapted to transmit light of a predetermined wavelength.

6. A measuring cell in accordance with claim 5, said cell comprising blocks closely engaging insulating material which surrounds the measuring body and a thermal capacitor having high thermal capacity,
said thermal capacitor also engaging the insulation around said measuring body for imparting a substantially even temeperature thereto,
said temperature essentially being the same as the temperature of the measuring medium and the reference medium, respectively.

7. A measuring cell in accordance with claim 6, wherein the thermal capacity of said thermal capacitor is utilized for equalizing the temperatures of the measuring medium and the reference medium in consequence of said mediums being in good thermal contact with said thermal capacitor.

8. A measuring cell in accordance with claim 6, wherein said blocks are adapted to convey a medium having a thermostatically controlled temperature, with a thermostatically controlled medium being utilized for thermostatic precontrol of said measuring and reference media by means of good thermal contact between said thermostatically controlled medium and said measuring and reference media.

* * * * *